(12) United States Patent
Peterman et al.

(10) Patent No.: US 10,254,229 B2
(45) Date of Patent: *Apr. 9, 2019

(54) PORTABLE WATER QUALITY INSTRUMENT

(71) Applicant: OndaVia, Inc., Hayward, CA (US)

(72) Inventors: Mark C. Peterman, Fremont, CA (US); Merwan Benhabib, San Francisco, CA (US); Samuel Kleinman, Oakland, CA (US)

(73) Assignee: OndaVia, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/198,163

(22) Filed: Mar. 5, 2014

(65) Prior Publication Data

US 2014/0186939 A1 Jul. 3, 2014

Related U.S. Application Data

(63) Continuation-in-part of application No. 12/589,365, filed on Oct. 21, 2009, now Pat. No. 8,702,976, which
(Continued)

(51) Int. Cl.
*G01N 21/65* (2006.01)
*B01L 3/00* (2006.01)
(Continued)

(52) U.S. Cl.
CPC ........ *G01N 21/65* (2013.01); *B01L 3/502761* (2013.01); *G01J 3/18* (2013.01);
(Continued)

(58) Field of Classification Search
CPC .......... G01J 3/4412; G01J 3/02; G01J 3/0256; G01J 3/0291; G01J 2003/2866;
(Continued)

(56) References Cited

U.S. PATENT DOCUMENTS 5,266,498 A * 11/1993 Tarcha ................. G01N 21/658
436/164
6,972,173 B2 12/2005 Su et al.
(Continued)

OTHER PUBLICATIONS

Jencks et al. Equilibrium isotop effects on the ionization of thiol acids. Journal of the American Chemical Society, 93:18 (1971) 4433-4436.*
(Continued)

*Primary Examiner* — Katherine Zalasky

(57) ABSTRACT

A hand-held microfluidic testing device is provided that includes a housing having a cartridge receiving port, a cartridge for input to the cartridge receiving port having a sample input and a channel, where the channel includes a mixture of Raman-scattering nanoparticles and a calibration solution, where the calibration solution includes chemical compounds capable of interacting with a sample under test input to the cartridge and the Raman-scattering nanoparticles, and an optical detection system in the housing, where the optical detection system is capable of providing an illuminated electric field, where the illuminating electric field is capable of being used for Raman spectroscopy with the Raman-scattering nanoparticles and the calibration solution to analyze the sample under test input to the cartridge.

7 Claims, 14 Drawing Sheets

Related U.S. Application Data is a continuation-in-part of application No. 12/082,094, filed on Apr. 7, 2008, now Pat. No. 8,070,956.

(60) Provisional application No. 60/912,681, filed on Apr. 18, 2007.

(51) Int. Cl.

| | | |
|---|---|---|
| *G01J 3/18* | (2006.01) | |
| *G01J 3/44* | (2006.01) | |
| *G01N 21/47* | (2006.01) | |
| *G01N 30/60* | (2006.01) | |
| *G01N 27/447* | (2006.01) | |
| *G01N 33/18* | (2006.01) | |
| *G01N 30/00* | (2006.01) | |

(52) U.S. Cl.
CPC ............ *G01J 3/44* (2013.01); *G01N 21/47* (2013.01); *G01N 21/4785* (2013.01); *G01N 21/658* (2013.01); *G01N 27/44704* (2013.01); *G01N 27/44791* (2013.01); *G01N 30/6095* (2013.01); *G01N 33/18* (2013.01); *B01L 2200/0652* (2013.01); *B01L 2200/12* (2013.01); *B01L 2300/0627* (2013.01); *B01L 2300/0636* (2013.01); *B01L 2300/0654* (2013.01); *B01L 2300/0681* (2013.01); *B01L 2300/087* (2013.01); *B01L 2300/0867* (2013.01); *B01L 2400/0418* (2013.01); *B01L 2400/0421* (2013.01); *G01N 30/6065* (2013.01); *G01N 2021/651* (2013.01); *G01N 2030/0095* (2013.01); *G01N 2201/0221* (2013.01); *G01N 2201/13* (2013.01)

(58) Field of Classification Search
CPC . G01J 2003/2879; G01N 21/47; G01N 21/49; G01N 21/62; G01N 21/658; G01N 21/63; G01N 33/18; G01N 2021/651; G01N 2021/656; B01L 2200/0652; B01L 2200/04; B01L 2300/0636; B01L 2300/0627
See application file for complete search history.

(56) References Cited

U.S. PATENT DOCUMENTS

| | | | |
|---|---|---|---|
| 8,070,956 | B2 | 12/2011 | Peterman et al. |
| 8,702,976 | B2 | 4/2014 | Peterman |
| 9,863,924 | B2* | 1/2018 | Peterman ............. G01N 21/658 |
| 2004/0058058 | A1 | 3/2004 | Shchegolikhin et al. |
| 2004/0110208 | A1 | 6/2004 | Chan et al. |
| 2004/0126279 | A1 | 7/2004 | Renzi et al. |
| 2004/0142484 | A1 | 7/2004 | Berlin et al. |
| 2004/0174520 | A1* | 9/2004 | Premasiri ............. C07D 471/04 356/301 |
| 2004/0191921 | A1 | 9/2004 | Farquharson et al. |
| 2006/0054506 | A1* | 3/2006 | Natan .................. B22F 1/0025 205/112 |
| 2006/0061762 | A1* | 3/2006 | Dwight et al. ................ 356/301 |
| 2006/0144786 | A1 | 7/2006 | Lin |
| 2006/0164636 | A1 | 7/2006 | Islam et al. |
| 2006/0166302 | A1 | 7/2006 | Clarke et al. |
| 2006/0240401 | A1 | 10/2006 | Clarke et al. |
| 2006/0257968 | A1 | 11/2006 | Van Duyne et al. |
| 2006/0260941 | A1 | 11/2006 | Tan et al. |
| 2006/0262303 | A1 | 11/2006 | Bonne et al. |
| 2007/0010026 | A1 | 1/2007 | Nguyen et al. |
| 2007/0059203 | A1* | 3/2007 | Burrell .................... G01N 21/65 356/301 |
| 2007/0127019 | A1 | 6/2007 | Zribi et al. |
| 2007/0155020 | A1 | 7/2007 | Su et al. |
| 2007/0224683 | A1 | 9/2007 | Clarke et al. |
| 2007/0236697 | A1* | 10/2007 | Zribi et al. .................... 356/454 |
| 2011/0266429 | A1 | 11/2011 | Vestel et al. |
| 2014/0260708 | A1 | 9/2014 | Harrell et al. |

OTHER PUBLICATIONS

Henderson et al. Appendix 1: Naturally occuring isotopes. Mass spectrometry of inorganic, coordination and organometallic compounds: Tools—Techniques—Tips. John Wiley & Sons, Ltd. (2005) 235-246.*
Ondavia, "Monoethanolamine (MEA) Analysis Cartridge," available at <https://www.ondavia.com>, accessed Jul. 11, 2017, 1 page.*
Ondavia, "Basic Analysis System," available at <https://www.ondavia.com>, accessed Jul. 11, 2017, 1 page.*
Marz et al., "Towards a quantitative SERS approach—online monitoring of analytes in a microfluidic system with isotope-edited internal standards", 2009, 232-242, No. 4, Journal of Biophotonics.
Zhang et al., "Isotope Edited Internal Standard Method for Quantitative Surface-Enhanced Raman Spectroscopy", 2005, 3563-3569, No. 77, Analytical Chemistry.
International Patent Application No. PCT/US2016/052178, International Search Report and Written Opinion dated Nov. 18, 2016.
Mark Peterman, "Rapid Contaminant Monitoring," OndaVia Inc., Oct. 2012, 27 pages.
U.S. Appl. No. 15/267,708, Non-Final Office Action dated Sep. 22, 2017.
U.S. Appl. No. 15/239,153, Non-Final Office Action dated Apr. 5, 2018.
U.S. Appl. No. 15/267,708, Notice of Allowance dated Nov. 15, 2017.
U.S. Appl. No. 15/792,165, Non-Final Office Action dated Apr. 9, 2018.

* cited by examiner (a)

(b)

(c)

PORTABLE WATER QUALITY INSTRUMENT

CROSS-REFERENCE TO RELATED APPLICATIONS

This application is a continuation-in-part of U.S. patent application Ser. No. 12/589,365 filed Oct. 21, 2009, which is incorporated herein by reference.

STATEMENT OF GOVERNMENT SPONSORED SUPPORT

This invention was made with Government support under contract IIP-1058590 awarded by National Science Foundation. The Government has certain rights in this invention.

FIELD OF THE INVENTION

The invention relates to fluid analysis. In particular, the invention relates to a hand-held microfluidic analysis device that can be used in remote applications.

Chemical mixture separation is important to many fields. While a variety of approaches exist for chemical separations, chromatography and electrophoresis are two of the most commonly used analytical methods.

Chromatography is a set of laboratory techniques used to separate constituents from a chemical mixture. Chromatography is used in everything from water and food safety to biotechnology and drug discovery. It is also a common technique used in standard laboratory procedures and cutting-edge scientific research, where liquid chromatography, size-exclusion chromatography, affinity chromatography and high-pressure liquid chromatography are traditionally used.

In liquid chromatography, the unknown sample is dissolved in a liquid mobile phase, which is then over a stationary phase. The analyte of interest remains with, or is slowed by, the stationary phase, separating it from the overall mobile phase mixture.

Liquid chromatography can be further divided by the stationary phase, comprising three methods: ion-exchange, size-exclusion, and affinity chromatography. In ion-exchange chromatography, the stationary phase contains charged functional groups, which interact with the charge on the analyte. This charge will affect the migration time through the chromatography system, separating the analyte from the overall sample.

Size-exclusion chromatography, or gel permeation chromatography, separates constituents based on size, passing the mobile phase through a porous medium that only passes particles below a certain size.

Affinity chromatography is based on selective covalent bonding with the mobile phase. For example, proteins or polymers tagged with a specific linker can be isolated with the appropriate linker analogue.

General improvements in liquid chromatography have increased the efficiency and resolution, leading to the more common description of high-pressure (or performance) liquid chromatography (HPLC). Such separations typically require macroscopic volumes of material—the mobile phase may be a few milliliters or more. Additionally, these separations can take hours to process. And, even with these drawbacks, the results are still rather crude single-monomer polymer separation across a broad stripe of analytes is a significant challenge.

An alternative to HPLC is electrophoresis, where charged molecules are separated in an electric field. FIG. 1 shows a prior art schematic illustration of electrokinetic flows 100. The electroosmotic 102 and electrophoretic 104 flows of particles 106 scale linearly with the electric field E by a mobility factor $\mu$ inside a channel 108, where the electric field is created by a voltage supply 110 across the length of the channel 108. The arrows are shown in opposite directions for illustration, where they may point in either direction depending on charges and material properties. This separation of the components of a mixture of charged molecules is an important scientific and technological process, including analytical methods such as DNA sequencing and preparative methods such as the purification of proteins. Successful separation of a mixture of polyelectrolytes by an applied electric field according to charge or mass depends on symmetry-breaking mechanisms between the driving force, related to the electric field, and the friction offered by the medium, such as a buffer solution with or without a matrix such as a gel. Accordingly, if the driving force and the friction force scale the same way with charge or length, the ratio of these quantities is then independent of charge or length, and separation is not achieved. There are many ways to achieve symmetry-breaking for polyelectrolytes such as DNA, ranging from the use of gel matrices for sequencing relatively short DNA fragments in a constant electric field, to pulsed-field gel electrophoresis for separating large DNA fragments, or to creating asymmetric molecules for separation in free solution.

There are multiple approaches to electrophoresis. Capillary electrophoresis separates components within a glass capillary. Here, the properties of microfluidic flow within such a capillary improve efficiency and reduce separation times. Known instruments can reduce the separation time to 30 minutes, while allowing the use of a few microliters of material. For fields where materials are expensive and rare, such as drug discovery, capillaries offer tremendous benefits.

Furthermore, in the last few years, microfabricated capillary electrophoresis devices have entered the market. These devices offer parallel processing with a few to dozens of simultaneous separations. Microfabricated devices also work with smaller sample sizes. These advantages are both increasingly important in biotechnology, as many samples are of limited material quantities. Commercial microfabricated capillary electrophoresis systems are being used for DNA sequencing, RNA analysis, protein separations, and even cell content studies.

The ability to separate a chemical mixture into constituents is absolutely necessary for all of analytical chemistry. Improvements in speed, quality, efficiency, or resolution of separation techniques are necessary enhance the behind-the-scenes laboratory work that ensures the quality of everyday products. These products can be categorized in the fields of pharmaceuticals, laboratory, environmental, food/beverage, and academic. Each of these segments has a broad impact across all of society, such as quality-control analysis, where imported food products must be analyzed for hazardous materials, or water and soil must be measured for pollutants before entering public consumption.

Many liquid chromatography methods are used in environmental analysis, such as water and soil quality analyses, where measuring organic compounds or mineral-content levels in water is handled by experienced lab technicians operating chromatography tools. These processes are expensive and time-consuming. Nevertheless, the application of chromatography in these fields is tremendous and pervasive.

Thus, the broader impact of new techniques to speed and improve chemical separations is wide-ranging and important.

While recent electrokinetic separations have improved separation speed and resolution for charged molecules over traditional chromatographic techniques, such improvements are still lacking for many particles including charged and uncharged molecules.

Capillary electrophoresis provides improvements in speed and resolution over LC. Furthermore, capillary electrophoresis works effectively in parallel systems and with microscopic volumes. When molecules are uncharged, electrophoretic methods have been ineffective, the options for separating such molecules are limited to older LC techniques, such as size-exclusion or affinity chromatography.

Uncharged polymers are important in many everyday products. For example, poly(ethylene glycol) is used in a multitude of medical applications: in laxatives, in skin creams and eye drops, and for delayed protein drug delivery. The polymer poly(vinyl alcohol) is used extensively in products ranging from children's putty to adhesives. Furthermore, under electrophoretic conditions, free-draining coils, such as DNA, are effectively uncharged as their drag-to-charge ratio is uniform, where DNA will not separate in an electric field without a symmetry-breaking mechanism. Additionally, many proteins and peptides are effectively uncharged; electrophoretic separation of these important biomaterials is not possible with additional processing steps. As uncharged polymers are necessary components of everyday materials, improved separations of these materials will improve the safety and quality of these products.

Accordingly, there is a need to develop hand-held low-cost microfluidic separation device separating charged and uncharged particles, where the method has broad applications in environmental, biotechnological, and chemical processing. A further need exists for such a device that provides detection resolution at the part-per-billion (ppb) level.

SUMMARY OF THE INVENTION

To address the needs in the art, a hand-held microfluidic testing device is provided that includes a housing having a cartridge receiving port, a cartridge for input to the cartridge receiving port having a sample input and a channel, where the channel includes a mixture of Raman-scattering nanoparticles and a calibration solution, where the calibration solution includes chemical compounds capable of interacting with a sample under test input to the cartridge and the Raman-scattering nanoparticles, and an optical detection system in the housing, where the optical detection system is capable of providing an illuminated electric field, where the illuminating electric field is capable of being used for Raman spectroscopy with the Raman-scattering nanoparticles and the calibration solution to analyze the sample under test input to the cartridge.

In one aspect of the invention, the chemical compounds can include thiols, amines, silanes, polymeric particles, metallic particles, crown esters, cysteamine, cystamine, diethylaminethanethiol, mercaptopropionic acid, 1-propanethiol, octanethiol, octyldecanethiol, polystyrene, iron, or silica.

According to another aspect of the invention, the calibration solution comprises isotopes of the sample under test.

In a further aspect of the invention, the calibration solution comprises a chemical composition in the sample under test.

BRIEF DESCRIPTION OF THE FIGURES

The objectives and advantages of the present invention will be understood by reading the following detailed description in conjunction with the drawing, in which.

DETAILED DESCRIPTION OF THE INVENTION

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

A new technique for separating uncharged and charged particles is provided, where the method has broad applications in environmental, biotechnological, and chemical processing. An electrokinetic approach is provided for the separation of uncharged polymers. Typically, uncharged molecules, such as certain peptides, proteins, and commercially important polymers, are not influenced by an electric field, although they will interact with a moving buffer solution. When this moving buffer solution has a spatially uniform velocity profile, the uncharged molecules will not separate by length or size. Conversely, when the moving buffer solution has a non-uniform velocity profile, molecules can be separated based on size.

Figure 1:
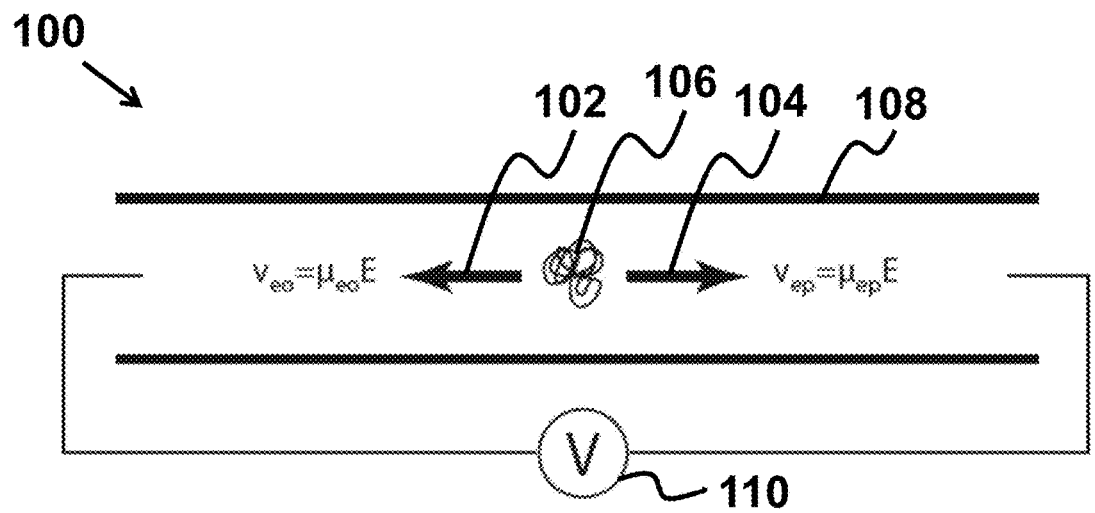
FIG. 1 shows a prior art schematic illustration of electrokinetic flows.
Figure 2:
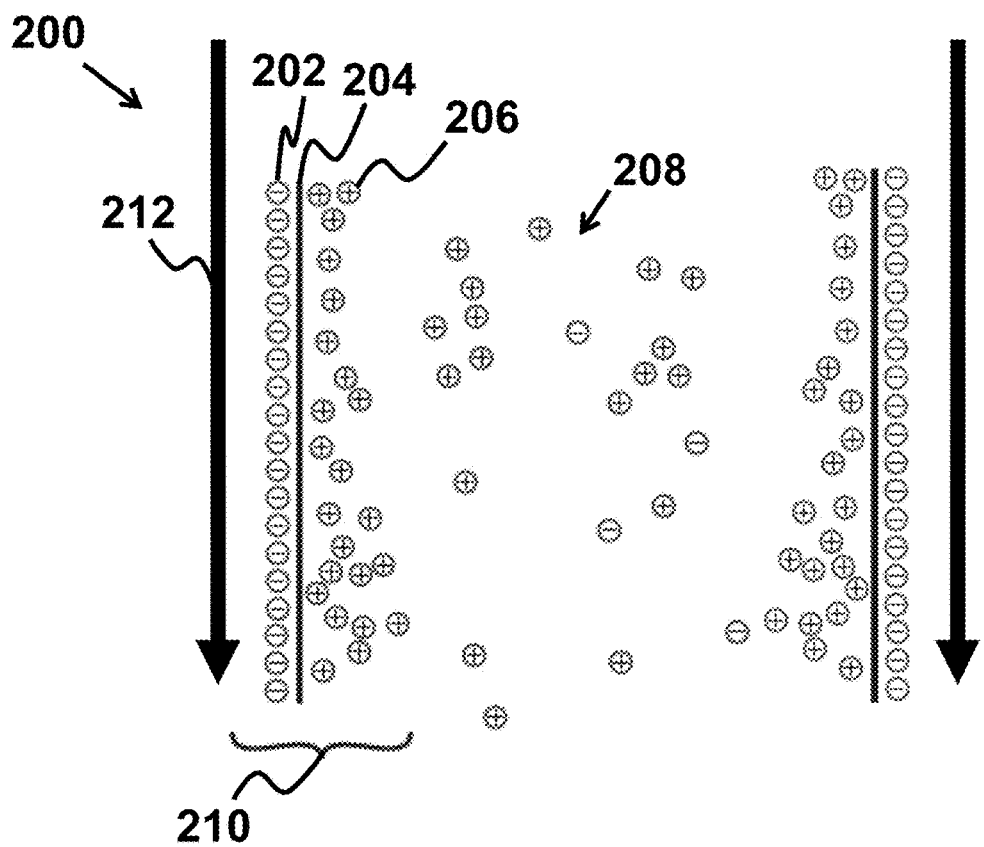
FIG. 2 shows an electric double layer leading to electroosmotic flow according to the present invention.

While an electric field does not affect uncharged molecules directly, it does give rise to a bulk flow of a buffer solution. This bulk fluid movement past a stationary solid surface, called electroosmosis, is due to the formation of a charged double layer at the solid-liquid interface. FIG. 2 shows a schematic drawing of an electric double layer providing electroosmotic flow 200. As shown a first charge layer 202 is fixed to channel wall surface 204, while the opposite charges 206 remain mobile in solution 208. At many liquid-solid interfaces, dissociated liquid ions, such as water ions, will interact with the solid surface, creating a charged double layer 210, where an applied electric field (not shown) is able to move the mobile ions 206 within the double layer 210, dragging the bulk solution 208 and any solvated molecules (not shown) along the microchannel 212. The solution can be water, phosphate buffered saline, TTE (0.5 M Tris, 0.5 M TAPS, 0.02 M EDTA) or any water-based solution.

According to the current invention, non-uniform electroosmotic flow provides separation of uncharged molecules in free solution. The current invention uses the properties of Brownian motion and how it affects the random motion of small molecules more than large molecules. Specifically, small molecules exhibit a higher probability of spending time away from the center of a channel having non-uniform electroosmotic flow than the large molecules, resulting in a longer average path length for the small molecules and contributing to a lower effective mobility. The current invention provides a method of enabling large molecules to exit the channel ahead of the small molecules, where the small molecules have a longer travel time through the channel.

As stated, a non-uniform electroosmotic flow is generated by varying the channel geometry along the x-axis, resulting in a distribution of velocities in the x-direction along the y-axis. As a particle moves along the y-axis, away from the center of the channel, the curved flow lines of the channel walls result in longer path lengths. Because the smaller molecules have a greater propensity to diffuse laterally, size-dependent separation occurs, where smaller molecules fall behind the larger molecules within the solution as they migrate along the column length. Conversely, the larger molecules tend to spend more time along the center of the channel and progress through the column at a faster rate.

Figure 3:
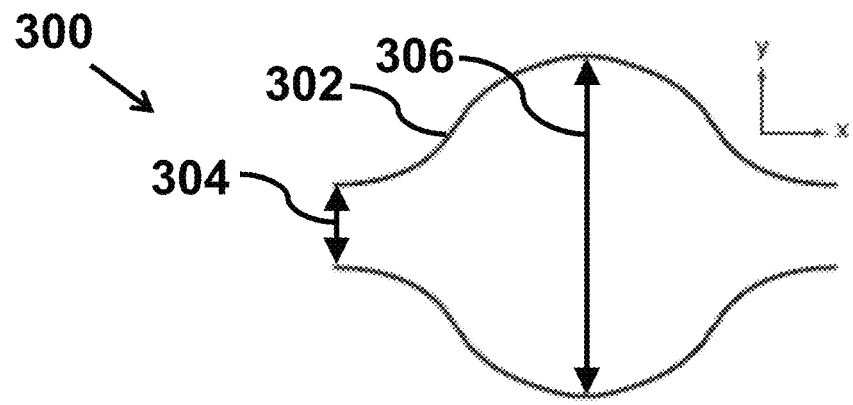
FIGS. 3a-3c show a channel geometry and flow diagram according to the present invention.
Figure 3:
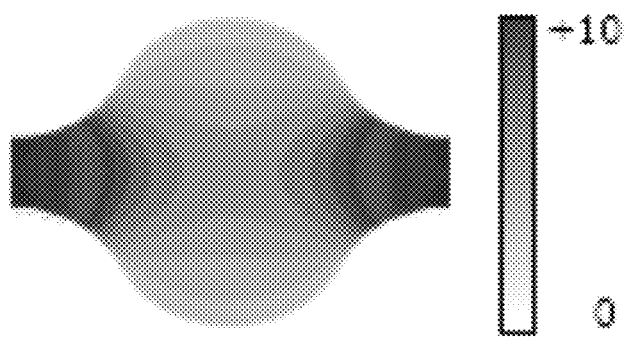
Figure 3:
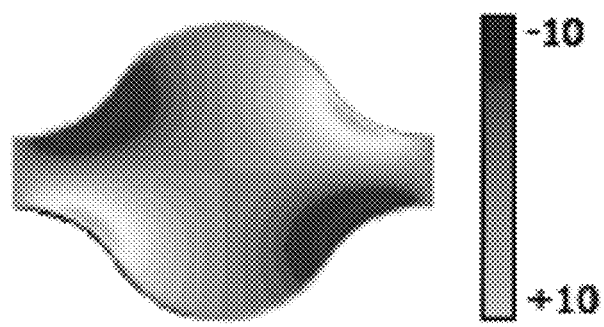

FIGS. 3a-3c show channel geometry and flow diagrams 300 according to one embodiment of the invention. FIG. 3a shows a non-uniform channel 302 having a narrow span 304 and a wide span 306, where a geometry parameter a is defined as the ratio of the widest 306 to narrowest 304 regions. Shown in FIGS. 3b and 3c are x-velocity and y-velocity results, respectively, from a finite element model.

Here, Navier-Stokes and momentum conservation equations are used, and a force term is added due to the applied electric field, where ρ is the fluid density, v is the velocity, μ is the viscosity, κ is the Debye length, p is the pressure, ε is the dielectric constant, ψ is the potential due to the electric double layer, and φ is the applied potential, giving:

$$\rho\left[\frac{\partial v}{\partial t} + (v \cdot \nabla)v\right] = -\nabla p + \mu\nabla^2 v + \varepsilon\varepsilon_0\kappa^2\psi\nabla\varphi$$

$$\nabla \cdot v = 0.$$

The total electric potential in the microfluid channel can be described as the sum of the electric double layer potential and the applied potential. The Debye-Hückel approximation is used to simplify the expression for ψ, allowing both electric potentials to be determined by Poisson's equation.

A finite element analysis software package was used with standard values for the density, dielectric constant, and viscosity of water, plus the Debye layer parameters ξ=−40 mV and κ=−1.13 μm. The solution was discretized on a 400×400 grid, and introduced into the polymer flow solver.

To demonstrate the efficacy of the current invention, the flow pattern was generated on four geometries. The flow for α=0.0, 1.9, 3.0, 4.1, and 7.0 were modeled, with each respective geometry repeated periodically. For each geometry parameter, the velocity was scaled at the channel center to the value for α=4.1. A parameter of unity corresponds to a constant flow rate across and along the entire channel, thus corresponding to a uniform electroosmotic flow.

The polymer flow was modeled using an exemplary discrete, worm-like chain model. The model consists of N beads of radius a connected by N−1 springs. For N beads, with positions $r_i$, the equations of motion are given by:

$$\dot{r}_j = \sum_{j=1}^{N} \overline{D}_{ij}\overline{F}_j + \overline{N}_i(t).$$

This equation was solved directly by a second-order Runge-Kutta method for stochastic differential equations. All motion in the z-direction was set to zero. The force acting on each bead, Fj, has three components: the Stokes' force from the moving fluid with velocity $v_j$ at the bead position, and the inter-bead spring and bending potentials, as provided in Volkel and Noolandi.

The fluid velocity was taken from the finite element model, with linear interpolation from the output grid to the particle coordinates. The constants from these equations are: bond length, b=2a; persistence length, P=5b; and spring constant, h=100b. The terms Ni(t) are Gaussian-distributed random numbers with zero mean and variance.

$$\langle N_i(t)N_j(t')\rangle = 2k_b T \overline{D}_{ij}\delta(t-t').$$

The Ni terms were calculated at each time-step using a Cholesky decomposition. The self-diffusion terms of the diffusion tensor are given by Volkel and Noolandi. For bead-bead hydrodynamic interactions, the terms are given by the Rotne-Prager approximation. For each geometric parameter a, the strings were modeled at each of the lengths L=5, 10, 15, 20, 25, 30, and 40 beads.

The first observation is the final position of the polymers as a function of length and geometry. Uniform flow (i.e., α=1) results in longer polymers traveling slightly less distance than shorter polymers. In contrast, as the geometry parameter increases, the longer polymers travel farther, with increasing separation based on length.

Figure 4:
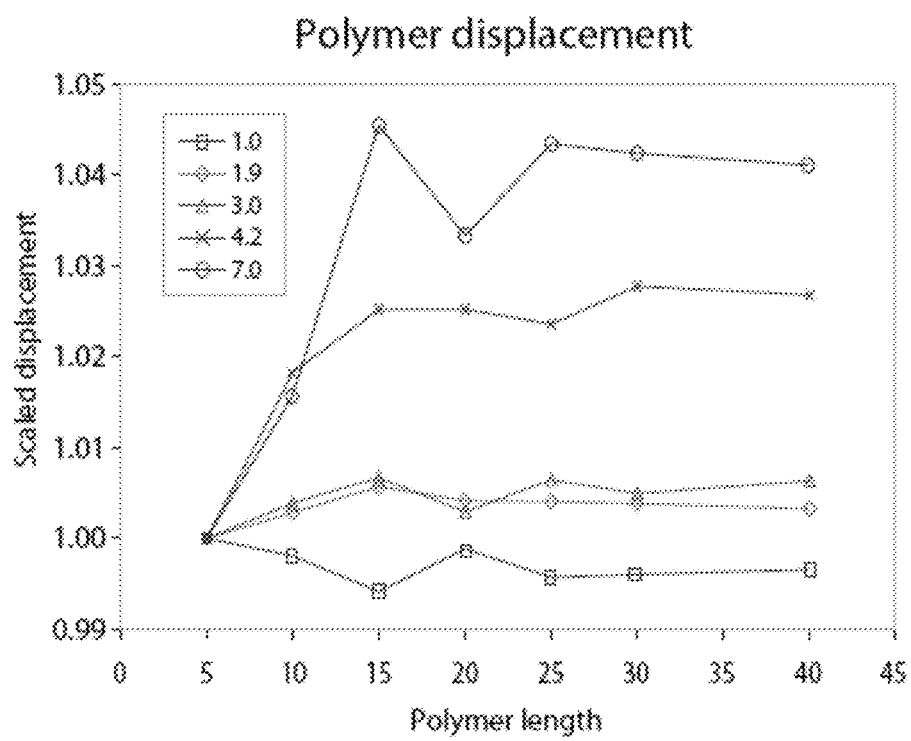
FIG. 4 shows numerical results on total polymer displacement of different channel geometries according to the present invention.

The position along the channel of representative polymers is illustrated in FIG. 4 that shows numerical results on total polymer displacement according to the current invention. For each geometry parameter, the symbol indicates the final position of the 5-bead string. While each geometry parameter results in the polymers moving different distances, the polymers end in regions with approximately the same velocity in the x-direction. Three representative flow lines are shown for $\alpha=4.1$.

Note, in contrast to a uniform flow field, longer polymers travel further than shorter polymers, and as the geometry parameter increases, the travel distance between short and long polymers increases.

Additional data illustrating the effects of polymer length on displacement is presented in FIG. 4. For the largest geometry parameter, the difference in distance between a 5-bead string and a 40-bead string is nearly 5%. This difference contrasts with the uniform flow situation, where the distance difference is close to zero.

The current invention provides a novel and powerful technique for the separation of charged and uncharged polymers. Capillary electrophoresis enables faster, more accurate and smaller sample size analysis over high-pressure liquid chromatography, but it only works with charged molecules. The current invention, unlike capillary electrophoresis, provides analysis of both charged and uncharged molecules.

Separation of uncharged polymers, where longer uncharged polymers will travel further along a channel than short uncharged polymers in non-uniform electroosmotic flow, enables polymer discrimination to single monomer resolution, according to the current invention. Single-monomer resolution separation of a poly(ethylene glycol) mixture is of critical importance to commercialization; if the device cannot separate the polymers with high resolution, the usefulness decreases.

Figure 5:
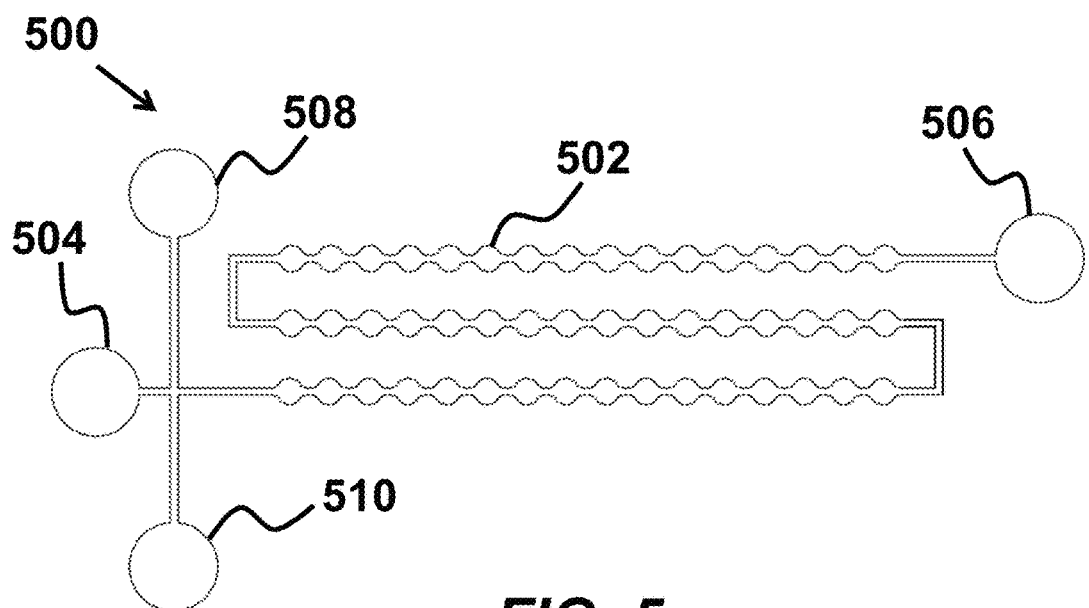
FIG. 5 shows a schematic of a device having a long region of undulary channels, coupled to inlet and outlet channels according to the present invention.

FIG. 5 shows a schematic of a device 500 having a long region of undulary channels 502, coupled to at least one inlet channel 504 and at least one outlet channel 506, according to the present invention. Sample insertion channels 508 are shown perpendicular to the inlet channel 504. A method of using electrokinetics for separating particles in a buffer solution is provided by the current invention. The column 502 has a non-uniform internal longitudinal cross-section, and the column can have a shape that can be linear, curved, circular, or spiral. At least one main inlet 504 and at least one main outlet 506 are provided, where the solution is input to the main inlet 504 and output from the main outlet 506. At least one sample inlet 508 and at least one sample outlet 510 are provided, where the particle (not shown) is introduced to the column 502 from the sample inlet 508 and fractionated samples are eluted from the sample outlet 510, whereby quality control and further analysis are enabled. An electric field is applied to the solution (see FIG. 7) in the column to generate a charged double layer (see FIG. 2) at a solid-liquid interface within the column, where the electric filed moves ions within the double layer, and a non-uniform velocity profile (see FIG. 3) is induced to the buffer solution, where the moving ions carry the particles along the column and the particles are separated according to size or charge.

According to one embodiment of the invention, the non-uniform channel 502 internal longitudinal cross-section has a generally counter undulating-shape profile, where the counter undulation is between a first wall cross-section and a second wall cross-section. The undulation can have a peak to peak distance in a range from 1 µm to 500 µm. Further, the undulation can have an undulation linear density ranging from 0.05 peaks/µm to 1 peak/µm. Further, the undulation first wall cross-section and the second wall cross-section have a ratio, or value of $\alpha$ with a widest separation and a narrowest separation that is greater than or equal to one.

In one exemplary aspect of the invention, the devices may be fabricated from glass wafers, such as Corning 7740. The surface chemistry of microfabricated glass devices is similar to capillaries, allowing the use of the same experimental techniques as used in capillary electrophoresis work. Other materials for electrophoresis can include molded plastic parts or other transparent wafers, such as quartz.

Figure 6:
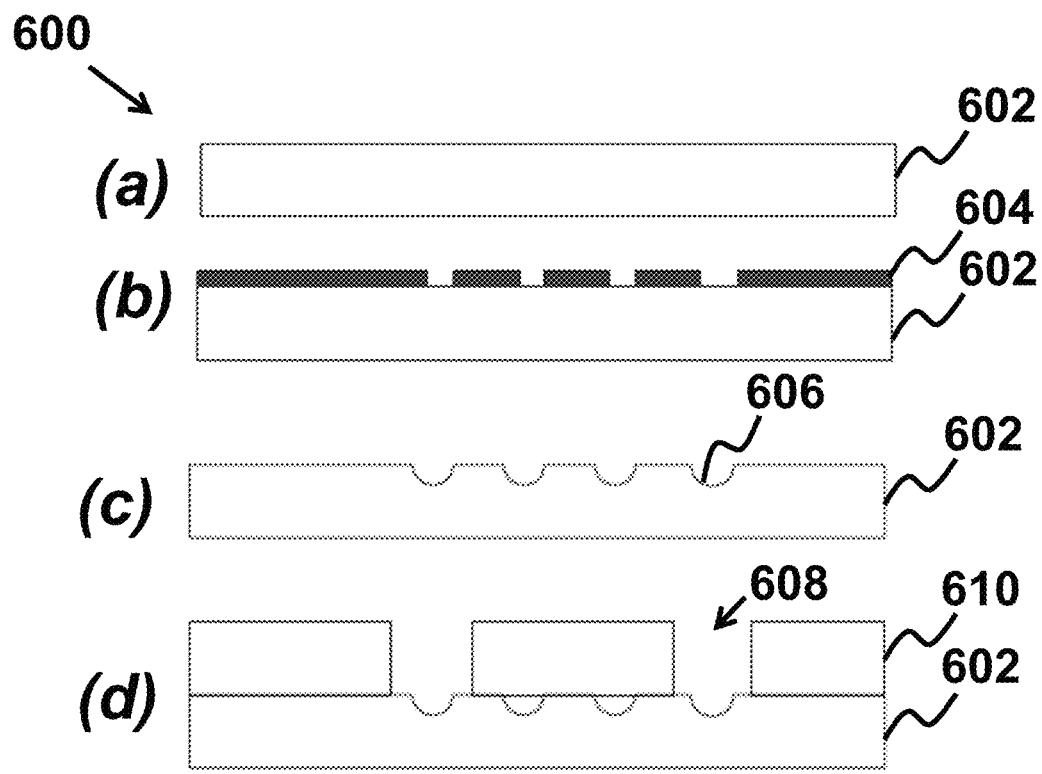
FIGS. 6a-6d show a process flow for fabricating a microfluid channel device according to the present invention.

FIGS. 6a-6d show a process flow for fabricating a microfluid channel device 600 according to the present invention. In FIG. 6a the process starts by providing a glass wafer 602 and applying a lithographic pattern photoresist 604 (see FIG. 6b) on the glass wafer 602. The wafers 602 are etched in a buffered oxide etch (see FIG. 6c), where the etched regions provide microfluidics channels 606. This etch is isotropic, creating half-cylindrical channels 606. A dry etch would result in a rectangular cross-section, if that were so required, according to one aspect of the invention. Access holes 608 are provided in a second glass-capping wafer 610 (see FIG. 6d). Once the wafers 602 are etched, the capping wafer 610 is aligned and thermally bonded thereto, according to one aspect of the invention. Unlike capillary electrophoresis, the current invention does not suppress electroosmosis, so internal channel coatings are unnecessary.

Figure 7:
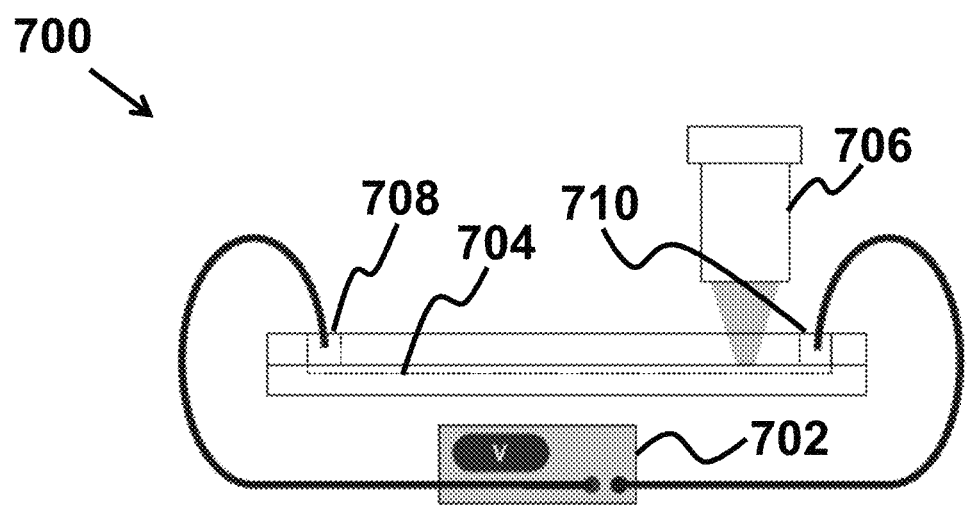
FIG. 7 shows a schematic drawing of a polymer separation apparatus according to the present invention.

FIG. 7 shows a schematic drawing of a polymer separation apparatus 700 according to one embodiment of the current invention. A high-voltage power supply 702 is used to drive the polymers (not shown) along the channel 704, while a fluorescence microscope 706 records the fluorescently-labeled polymers as they pass. It should be understood that there are numerous possible methods to identify and record the polymers within the apparatus, some examples include fluorescence, Raman spectroscopy, amperometry, color, or mass spectrometry which are embodied in the current invention.

As an example operation, a polymer containing solution is introduced to the main undulary channel 704 (see FIG. 6 for example) from the side injection channel 708. A voltage is applied along the main channel 704, allowing the polymers to travel down the channel 704. A change in charge may affect the flow rate, which can effect the retention time. By normalizing to the flow rate, a normalized retention time becomes the same for each run. This information enables quantitative measurement of polymer length based on transit time, according to one aspect of the current invention. The particles can have a particle size ranging from 1 nm to 500 µm.

The current invention provides a microfluidic separation device that is useful for surface-enhanced Raman spectroscopy (SERS) and other detection methods. Raman spectroscopy in general provides a chemical signature for a compound, but the Raman signal is generally too weak for part-per-billion detection levels. However, when a metallic nanoparticle that is smaller than the wavelength of light is introduced into the sample, the illuminating electric field will create surface plasmon resonances if there are free electrons in the nanoparticle, where the nanoparticle can be gold, silver, or copper beads, for example. These oscillating charges create an enhanced local electric field along certain directions. This field results in a much stronger Raman response. SERS experiments are often characterized by "hot spot" regions. Here the SERS signal reaches single-molecule detection capabilities. These regions are most likely due to nanoparticle to alignments that create even larger electric field enhancements.

Using SERS for analyte detection has been under study. It is believed the large signal enhancement creates new opportunities to measure very small concentrations: picomolar, femtomolar, and potentially even single molecules. The challenge with SERS is creating an interaction between the analyte and the metal surface. The highest-sensitivity studies rely upon binding events to bring the molecules into close contact. While very sensitive, this approach is limited to measuring a previously decided set of analytes for which the nanoparticles are prepared. The binding does not need to be specific; for example, treatments with octadecylthiol have been used successfully for SERS on planar substrates.

Figure 8:
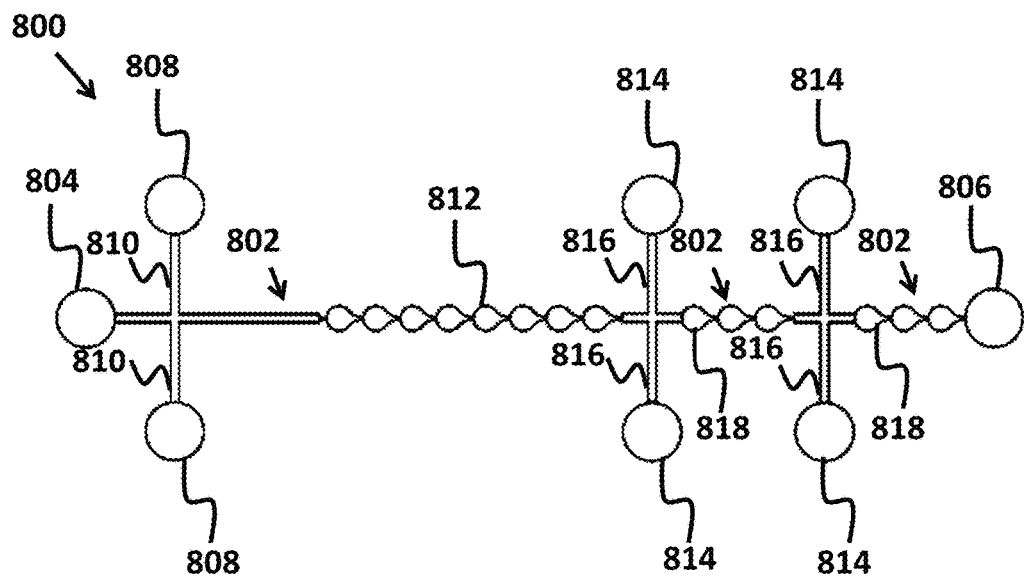
FIG. 8 shows a top view of one embodiment of the microfluidic mixing device according to the present invention.

According to one aspect or the current invention, a sensitive detection system incorporated in a portable device is provided. The invention includes packing sections along a microfluidic separation channel with nanoparticles, for example gold nanoparticles, at a high density. The invention creates many hot spots simply through particle density. The invention uses microfluidic delivery and narrow channel geometries to trap signal-enhancing particles at a detection location within a longer separation channel. Referring now to the figures, FIG. 8 shows a top view schematic of a microfluidic separation device 800 having a main channel 802 spanning from a fluid input 804 to a fluid output 806. The microfluid separation device 800 includes at least one sample loading port 808 connected to the main channel 802 by a sample loading to channel 810. Separation regions 812 are disposed down stream from the sample loading channel 810. The invention further includes at least one detection particle loading port 814 connected to the main channel 802 by a detection particle channel 816. At least one detection region 818 is disposed down stream from the detection particle channel 816. As shown in the exemplary device of FIG. 8, the main channel 802 is intersected by two perpendicular sample loading channels 810 to load the sample under study into the main channel 802, while the detection particle channel 816 is for loading the nanoparticle markers into the main channel 802.

Figure 9:
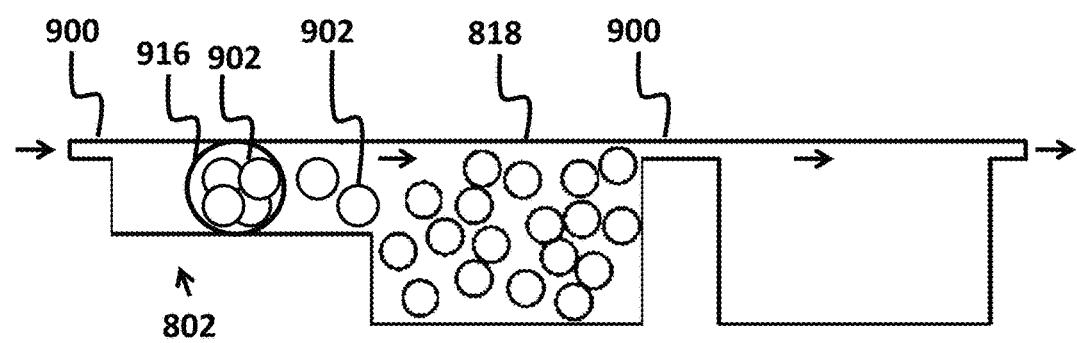
FIG. 9 shows a side cutaway view of a detection region of the microfluidic device in FIG. 1 according to the present invention.

FIG. 9 shows a side view of a detection region 818 of the microfluidic mixing device 800 in FIG. 8 according to the present invention. Proximal to the intersection of the detection particle channels 816 and the main channel 802 are geometric constrictions 900 that trap the nanoparticles 902 within the detection region 818. Further shown are arrows to indicate the flow direction of the fluid within the microfluid separation device 800. The fluid moves the nanoparticles 902 along the flow path to compact them within the detection region 818. The current invention relies purely on proximity by creating a region densely packed nanoparticles 902. According to one exemplary structure of the invention, tight packing density (close-packed spacing) predicts a maximum volume ratio of 74% spherical nanoparticles for a microfluidic channel region 818 that is 50 µm in length and has a 25 µm width and depth, loaded with 40-nm gold nanoparticles 902, this type of volume packing will have a surface area nearly 700 times greater than the surface area of the channel region. Furthermore, the narrow regions between nanoparticles 902 with the non-linear path through the matrix will increase interactions. The current invention provides a sensitivity requirement of detecting materials in parts per billion.

In the base configuration of the current invention, included is a main channel 802 with at least one crossing sample loading channel 810 and at least one nanoparticle loading channel 816, and the detection region 818. The detection region 818 has geometric constraints 900 that prevent particles 902 of a certain size from entering the main channel 802 in either direction, or from continuing past the detection channel 818. The nanoparticles 902 may be metallic, such as gold, copper, silver, fluorescent particles, magnetic particles, particles having binding chemistry, latex particle, polystyrene particles or quantum dots for surface-enhanced Raman scattering. According to one aspect, the particles are on the order of 10 nm to 10 µm. The particles 902 may also be fluorescent beads designed to bind with an analyte of interest for an ELISA-type signaling approach. These particles can be loaded using any type of fluid driving mechanism such as electroosmosis, electrophoresis, fluid pressure, moveable wall pressure, undulary electroosmosis, undulary electrophoresis, undulary fluid pressure or undulary moveable wall pressure. Note that between the sample input channel 810 and detection region 818 can be a separation region 812 that isolates individual compounds (undulary electroosmosis, electrophoresis, or chromatography) before entering the detection region 818.

It should be apparent there are many geometries may be used to create these detection regions 818. The constrictions 900 can occur in the vertical direction, reducing the size of the detection region 818 from top to bottom. This approach requires etching short depths or sacrificial layers. The constrictions 900 can also occur in the horizontal direction, which would rely upon lithographic abilities to define the narrowest gaps.

According to one aspect of the invention, the Raman signal can be further increased by using chemistries, both non-specific and specific, to bind analytes to the nanoparticles 902. With over a billion nanoparticles 902 in each detection region 818, along with multiple detection regions 818, a separation column 802 could hold a large number of modified nanoparticles 902. For example, with five detection regions 818, each holding two hundred different bindings, this system 800 could detect one thousand compounds while maintaining greater than five million nanoparticles 902 per region.

Figure 10:
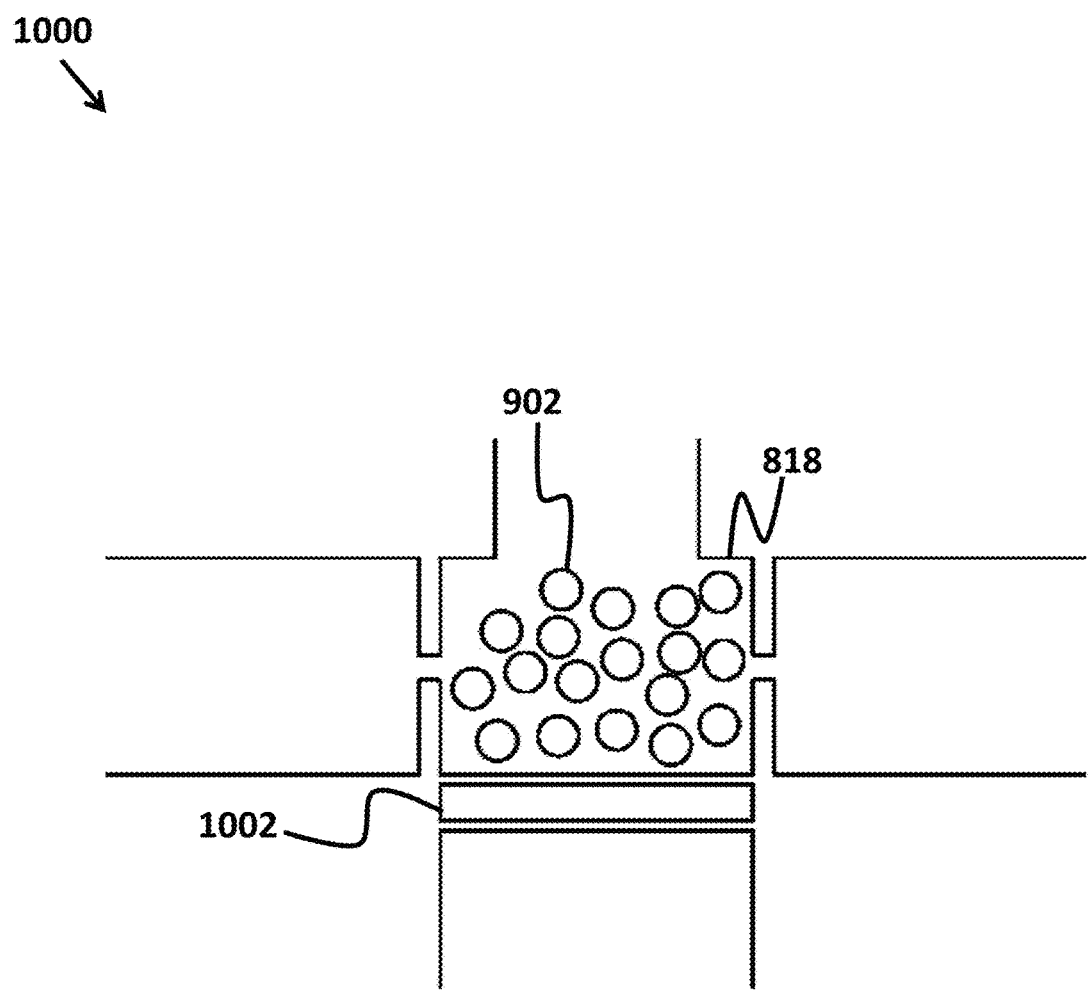
FIG. 10 shows a top view of a detection region with a liquid sieve at one end according to the present invention.

FIG. 10 shows an alternate embodiment 1000 of the invention, where the detection region 818 includes a sieve material 1002 that allows the carrying fluid to continue moving but stops the detection particles 902. For example, a molecular sieve will allow water to pass under pressure through atomic level openings in the material, but will block passage of larger particles.

Figure 11:
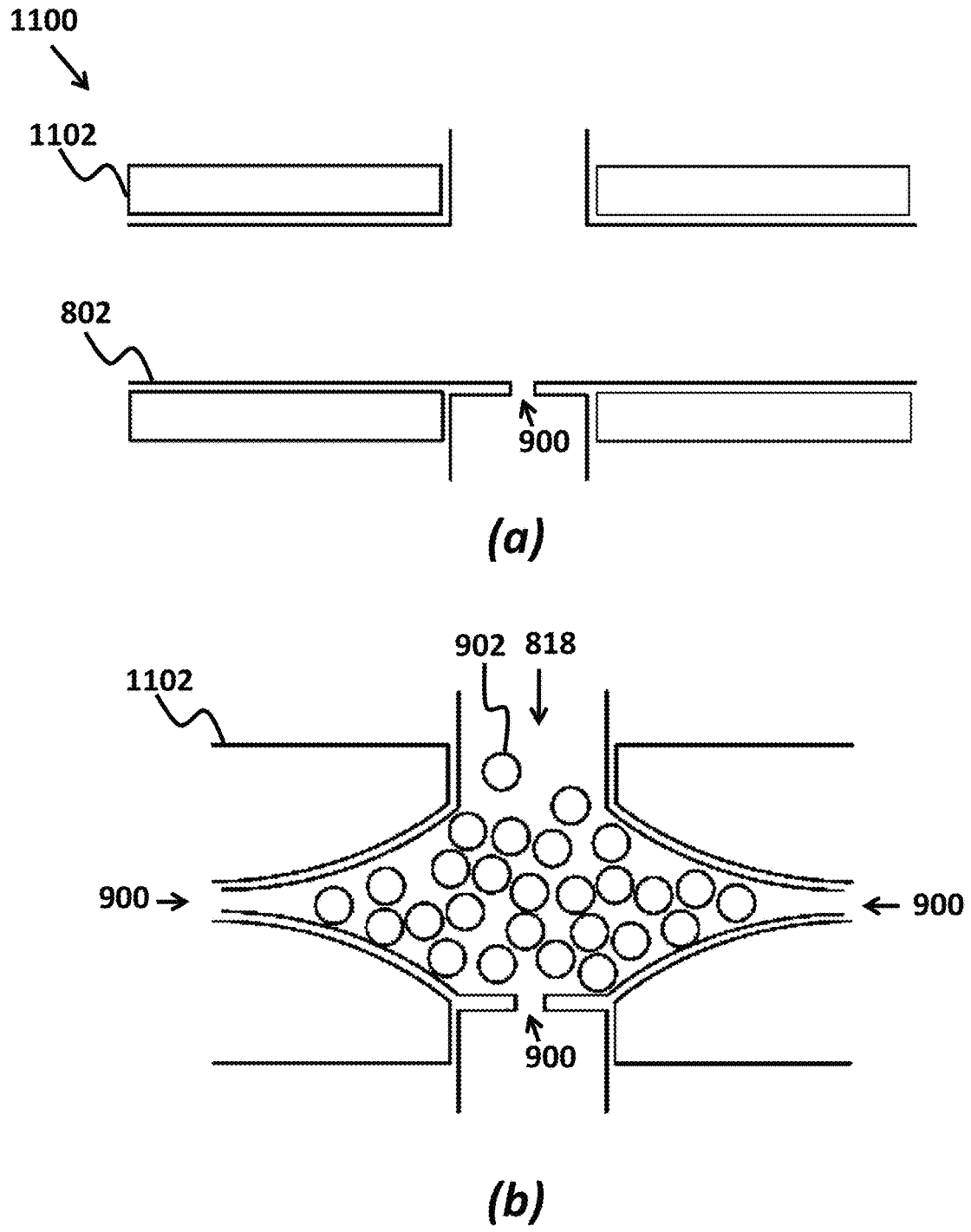
FIGS. 11a-11b show flexible microfluidic walls in an unconstructed state and in a constricted state according to the present invention.

FIGS. 11a and 11b show another embodiment of the invention 1100 that includes a reconfigurable detection region. According to the current embodiment 1100 the main channel 802 can be constructed from a flexible material, such as silicone elastomers. If a bladder region 1102 was placed in near proximity to the main channel 802, any pressure applied to the bladder 1102 will expand into the main channel 802, and provide a constricting region 900 to the channel 802. This approach allows for detection regions 818 to be repeatedly created and released, thus allowing for repeated use with different detection particles. It also allows one generic design to use particles 902 of different sizes, as the channel can be configured for any size constriction.

Figure 12:
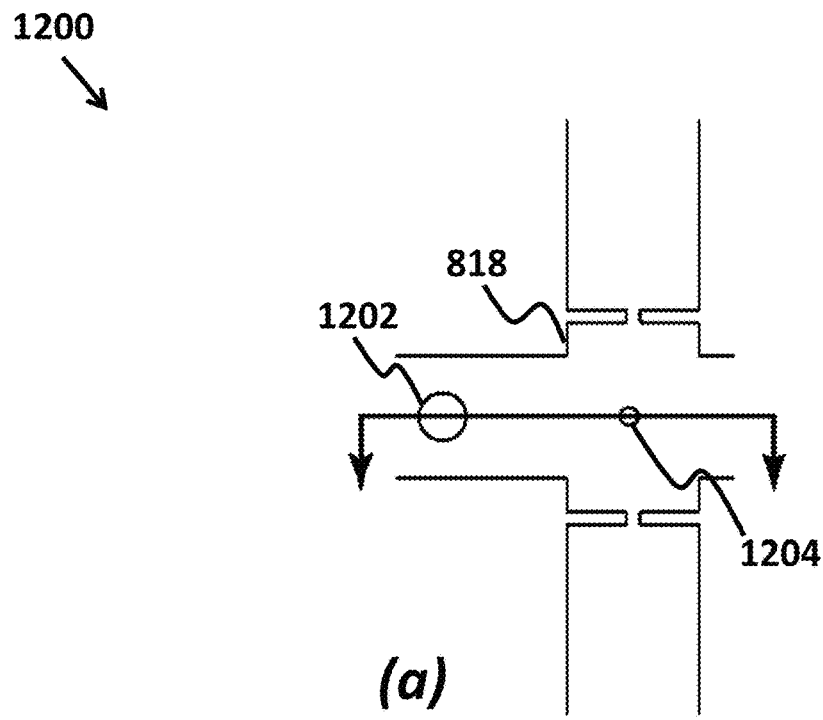
FIGS. 12a-12c show an alternative form of nanoparticle delivery according to the present invention.
Figure 12:
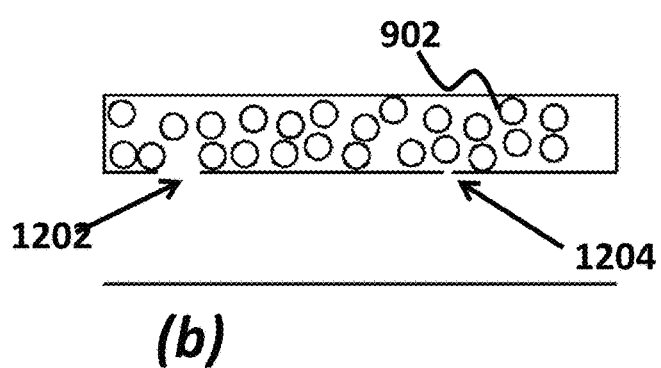
Figure 12:
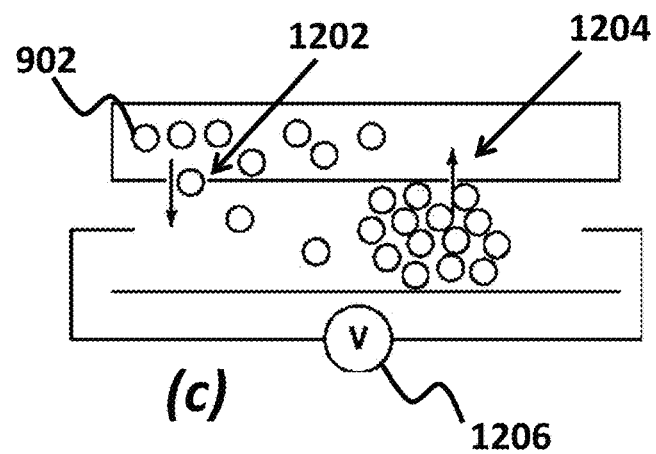

FIGS. 12a-12c show a further embodiment 1200 for supplying particles 902 to a detection region. FIG. 12a shows a top view of the current embodiment 1200 that includes an annotation to indicate the centerline of the cutaway views in FIGS. 12b and 12c. According to the figures, a third dimension is considered. Here, the top surface of the detection region 818 contains a first aperture 1202 that is large enough to pass particles 902 and a second aperture 1204 that is smaller than the particles. When an electric potential 1206 is applied along the detection region 818, the fluid and particles 902 will flow out of the first aperture 1202 by electroosmosis. The fluid will flow back through the second aperture 1204, but the particles 920 will not pass. This method creates local high density of particles 902 at the second aperture 1204.

According to one aspect the invention is for use in the field of water analysis. An exemplary system provides a method and device for on-site, field-based analysis of aqueous samples. Existing water measurements require collecting samples at a variety of locations, returning those samples to a laboratory, and processing the samples to find constituents. The process is time-consuming and expensive, resulting in many contaminants never being considered.

The system according to the current invention allows measurements on-site, providing analysis of hundreds or thousands of analytes in one test. A technician collects a water sample, processes that sample for analysis, and then introduces the sample to the cartridge. The cartridge is inserted into a housing, and appropriate analysis options are chosen through the user interface. Optics and electronics within the housing process the sample, analyze and measure the water constituents, and provide specific, quantitative feedback to the technician regarding all water contaminants.

The use of Raman spectroscopy, for example, provides a specific fingerprint for a wide variety of compounds. Coupling with additional optical and electrical measurement techniques allows better, faster, and more accurate analysis. The data resulting from the analysis provides information on a large number of analytes, eliminating the need for tedious, repetitive, expensive laboratory processing.

In some cases, users are interested in measuring one or more contaminants. For example, oil refineries are closely regulated for certain heavy metals, such as selenium, mercury, and lead. Agricultural users need to monitor the water applied to crops to avoid microorganism contamination. In one aspect of the invention, the cartridge and housing are modified for these specific measurements through selection of detection particles and optical measurement techniques. These modifications speed analysis and improve sensitivity.

In another aspect of the invention an option for food analysis is provided. Concerns continue to grow over contamination in our food supply. Food received from overseas sources might not meet required standards; fruits and vegetables can be contaminated with microorganisms such as *E. coli*; consumers may have allergies to specific foods. The housing and cartridge are modified to measure and report on these food contaminants. The user dissolves a food sample in a buffer solution before analysis. Instead of providing specific quantitative feedback, the system provides a "go/no-go" result indicating the presence of a contaminant of concern.

Figure 13:
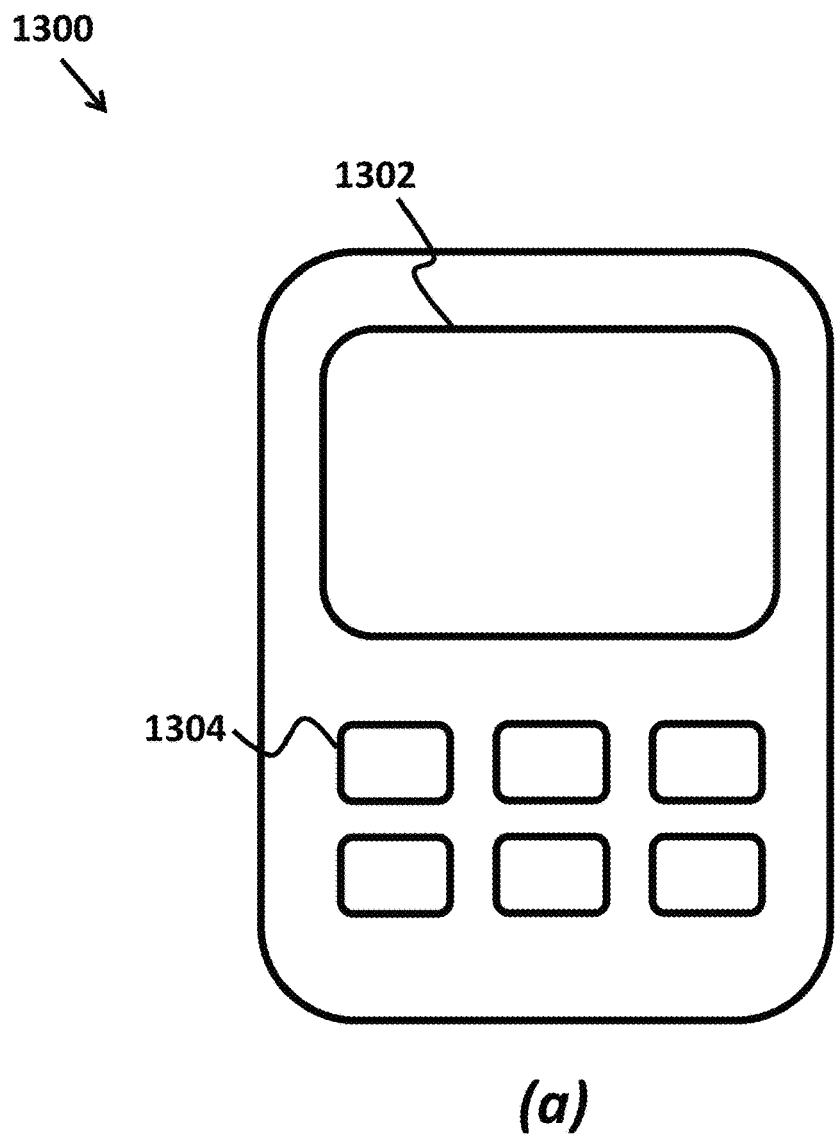
FIGS. 13a-13b shows a front view and a bottom view, respectively, of the analysis instrument, illustrating a screen to present information to the user and buttons for user input, and a slot for inserting the analysis cartridge according to the present invention.
Figure 13:
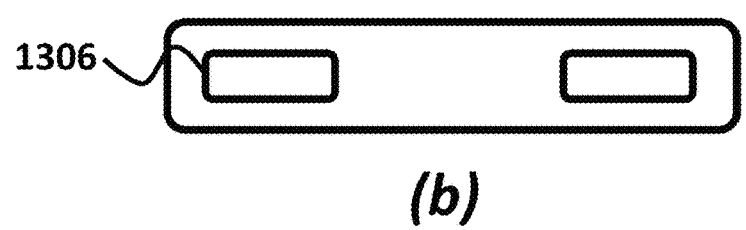
Figure 17:
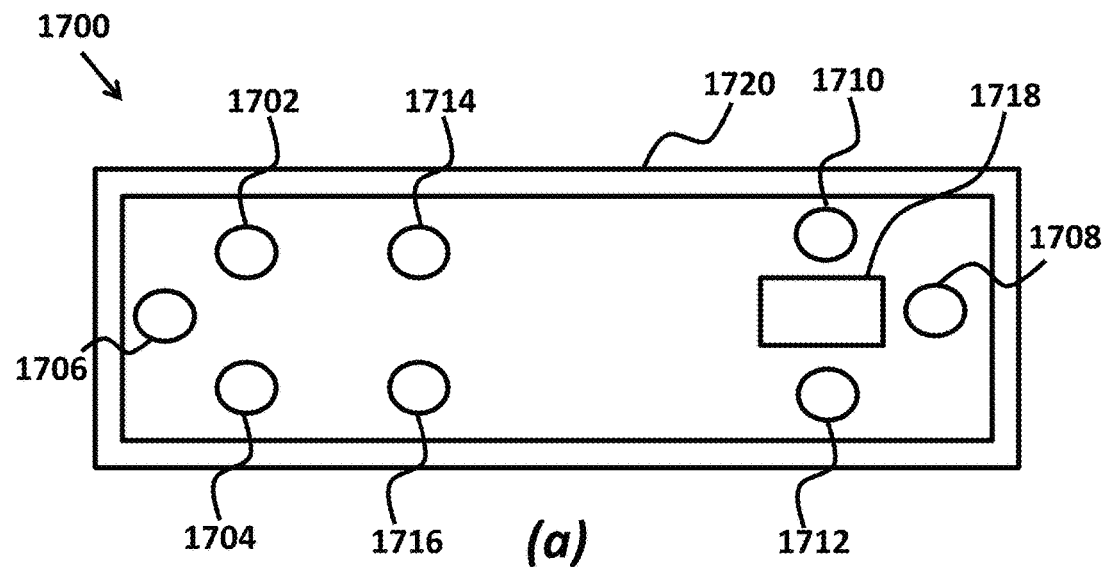
FIG. 17a-17b show a top view of the analysis cartridge and a side view of the shell, chip base, chip lid, sealing gasket, and protective film, respectively, according to the present invention.
Figure 17:
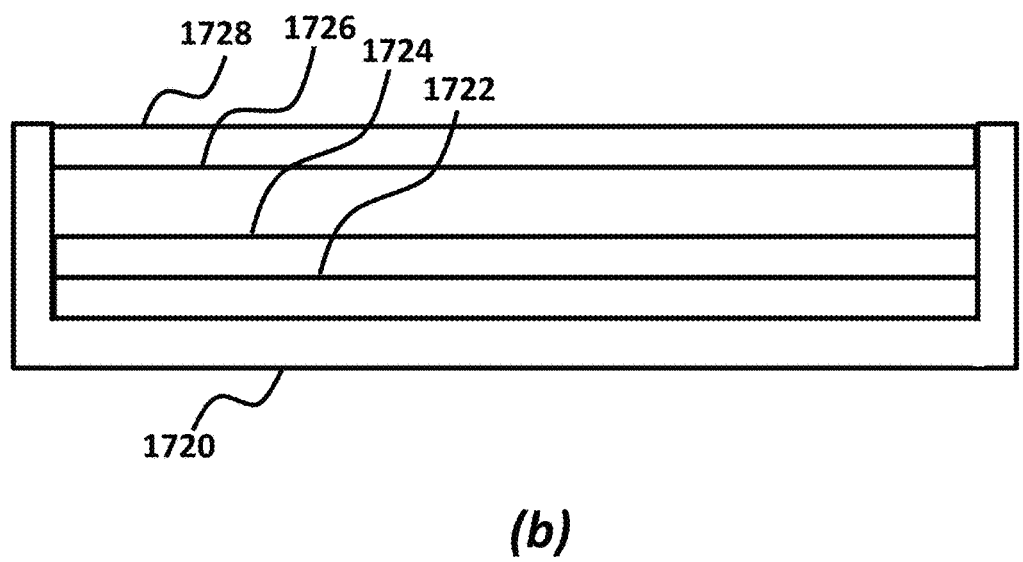

FIG. 13a shows a front view of the analysis instrument 1300, illustrating a screen 1302 to present information to the user and buttons 1304 for user input. FIG. 13b shows a bottom view of the instrument 1300, illustrating at least one cartridge input slot 1306 for inserting the analysis cartridge (see FIG. 17).

Figure 14:
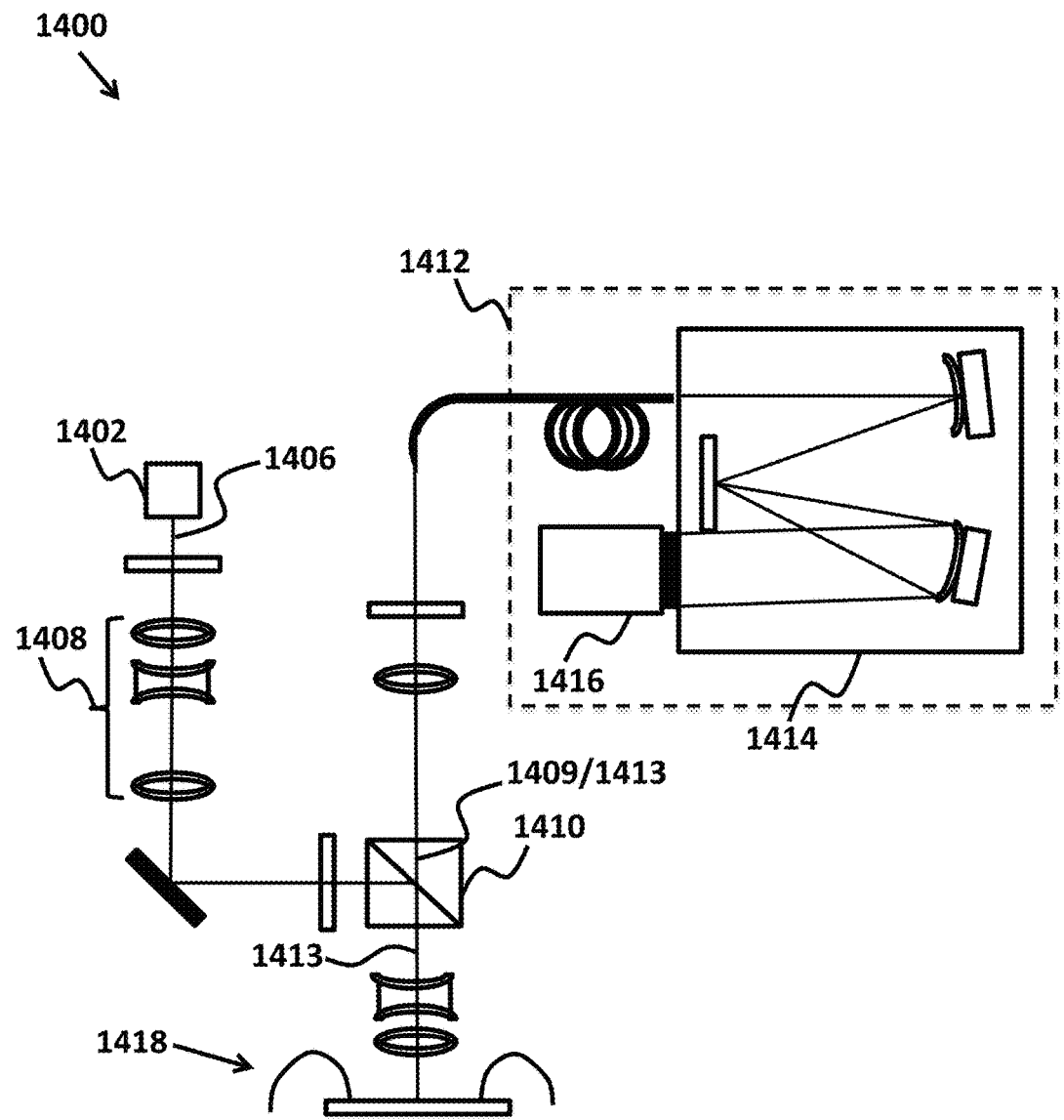
FIG. 14 shows an example optical system contained within the analysis instrument according to the present invention.

FIG. 14 shows an example optical system 1400, contained within the analysis instrument 1300. Shown is a light source 1402, such as a laser, projecting a light beam 1406 passing through a series of optics 1408 arranged as a beam expander that is reflected into a dichroic optic 1410 to direct the reference light beam 1411 into a spectrometer 1412 for analysis in a monochrometer 1414 and recordation in a CCD array 1416. The dichroic 1410 simultaneously directs the signal light beam 1413 to the cartridge 1418 to gather a signal from a sample in the cartridge 1418 and reflect the signal along the beam path into the spectrometer 1412 and CCD 1416 array for analysis.

Figure 15:
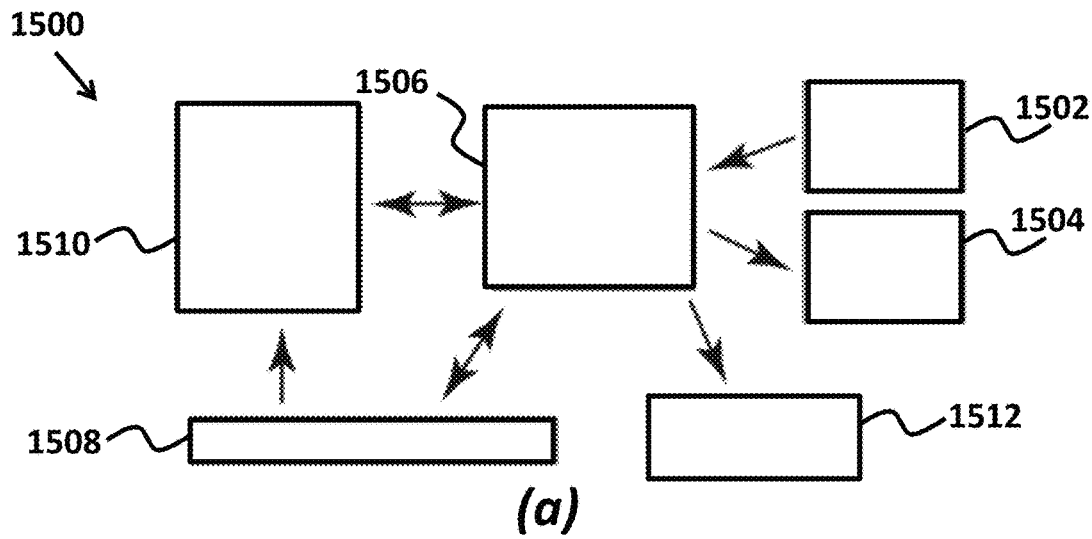
FIGS. 15a-15b show a block diagram presenting the system subcomponents and a flow chart of the system use according to the present invention.
Figure 15:
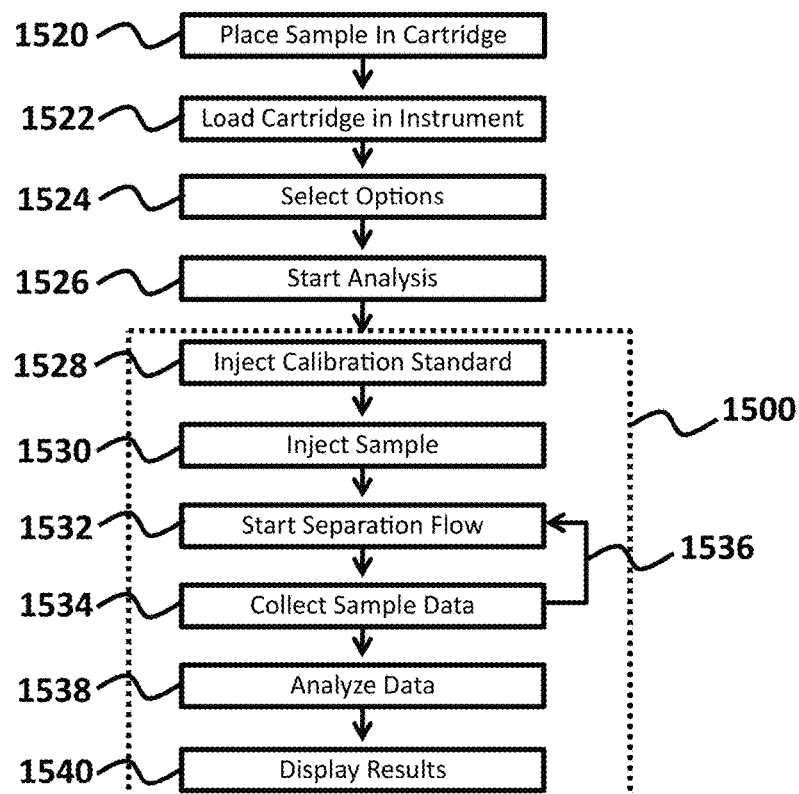

FIG. 15a shows a block diagram presenting the system subcomponents 1500. The instrument provides a user input 1502 for inputting samples, control agents, nanoparticles, etc. and selecting analysis options. The system further includes a user output 1504 for outputting the samples, control agents, nanoparticles, etc. and displaying, printing or outputting system results. Control electronics 1506 monitor system integrity and performance, operate the electric field applied to the cartridge 1508, and operate the optical system 1510 that optically reads data from the cartridge 1508 according to the optical system 1510 as described above. The control electronics 1506 digitize and process the optical data, presenting the results to the user on an external interface 1512. The control electronics 1506 and external interface 1512 further provide connectivity with external devices for data transfer, through various means such as wireless or wired connections.

FIG. 15b. A flowchart illustrating system use that includes placing the sample in the cartridge 1520, loading the cartridge in the instrument 1522, selecting the analysis options and starts the analysis 1526 by the system 1500. The analysis options can include expected contaminants, measurement accuracy, or analysis time, plus sample information for data tracking, such as location, temperature, quantity, user, or other test identification information. When the system 1500 is started, a calibration standard is injected 1528, then the sample is injected 1530 and the separation flow is started 1532 and optical data and other date is collected 1534, where separation flow 1532 and data collection 1534 iteratively continue 1536 until completion. The data is analyzed 1538 and the results are presented 1540.

Figure 16:
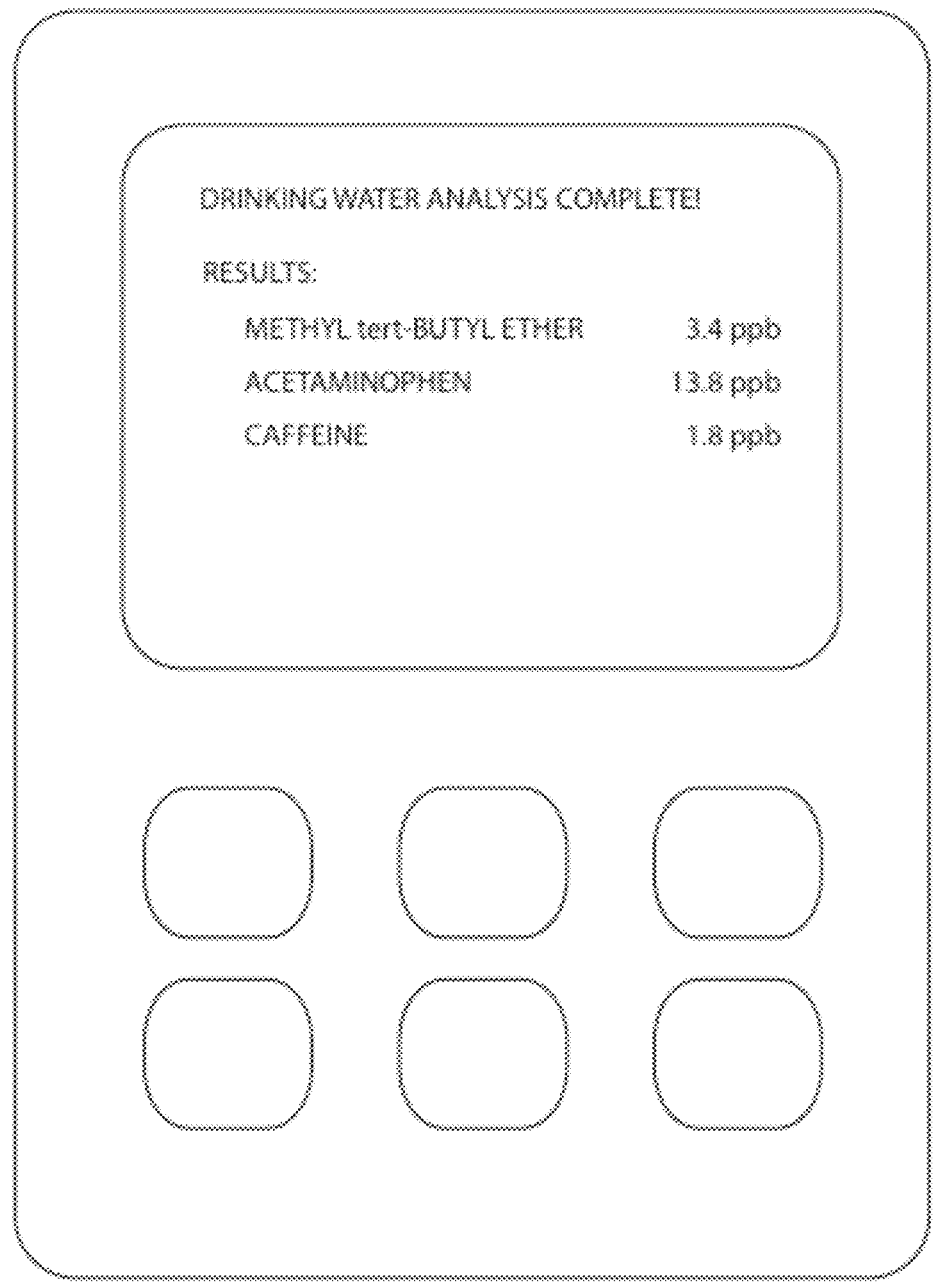
FIG. 16 shows an example of data presented to the user according to the present invention.

FIG. 16 shows exemplary data 1600 presented to the user.

FIGS. 17a-17b. show top and side views of the analysis cartridge 1700, respectively. FIG. 17a shows a top view having at least one sample inlet 1702 and at least one sample outlet 1704, in addition to at least one buffer inlet 1706 and at least one buffer outlet 1708. Further shown is at least one detection material inlet 1710, at least one detection material outlet 1712, at least one calibration standard inlet 1714, at least one calibration standard outlet 1716 and a detection window 1718 disposed above the detection region of the channel, as described above, where the analysis cartridge is surrounded by a protective shell 1720. FIG. 17b shows a side view of the analysis cartridge 1700 where the analysis chip is surrounded by the protective shell 1720, that holds chip base 1722, a chip lid 1724, a sealing gasket 1726, and protective film cover 1728.

According to another embodiment of the invention, the use of calibration standards is an important procedure for chemical separations and chemical analysis. Calibration standards provide a reference point against which data may be compared to provide accurate quantitative results.

For example, in chromatographic separations, chemicals with known retention times may be added to the solution under analysis. As these chemical elute from the chromatographic column, their elution time provides a scale against which the elution time of unknown species may be compared. Effectively, calibration standards provide a ruler for calibrating the elution time.

Calibration standards are also useful as a ruler for signal intensity. When a known amount of calibration standard is introduced to a sample, the quantity of unknown materials may be determined by comparing the measurement intensity, often through ratiometric methods.

The current embodiment of the invention provides calibration standards for chemical analysis using Raman spectroscopy and hand-held microfluidic testing devices. The introduction of calibration standards at device manufacturing or during analysis creates a powerful, quantitative chemical analysis system. For example, one analytical method that has been greatly hindered by a lack of reproducibility and accuracy is surface-enhanced Raman spectroscopy. Surface-enhanced Raman spectroscopy relies upon nanoscale metallic nanoparticles (i.e., markers) to provide an amplified Raman response. The current embodiment of the invention provides for calibration standards that greatly improve the reproducibility and accuracy of these surface-enhancing nanoparticles.

Figure 18:
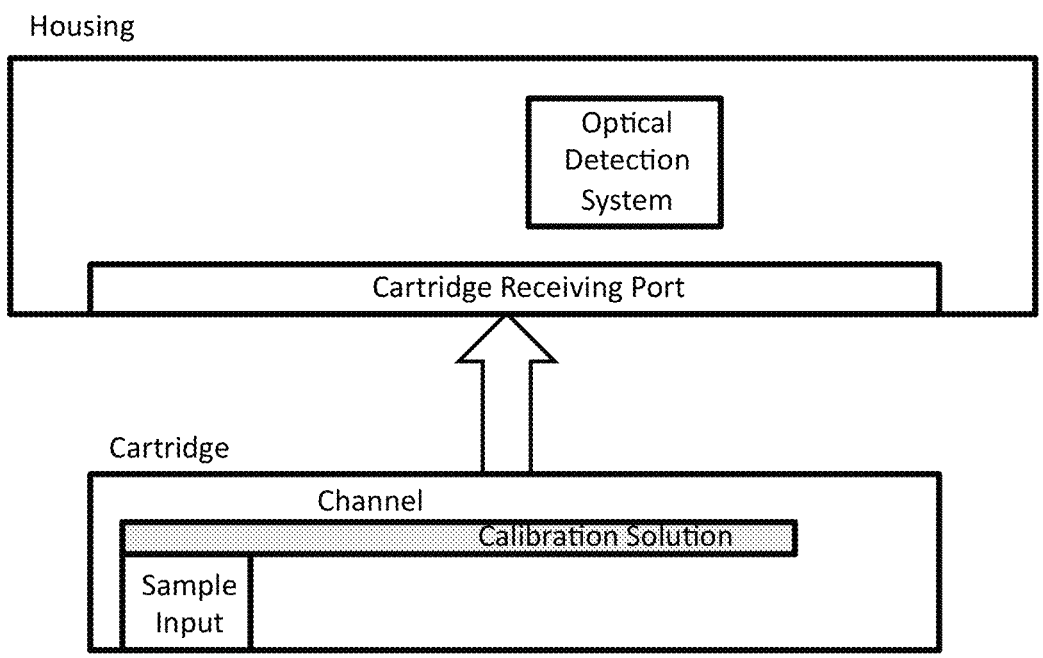
FIG. 18 shows a hand-held microfluidic testing device having a housing and cartridge, where the cartridge shows a calibration solution in the channel, according to one embodiment of the invention.

FIG. 18 shows a hand-held microfluidic testing device, according to one embodiment, that includes a housing having a cartridge receiving port, a cartridge for input to the cartridge receiving port having a sample input and a channel, where the channel includes a mixture of Raman-scattering nanoparticles and a calibration solution, where the calibration solution includes chemical compounds capable of interacting with a sample under test input to the cartridge and the Raman-scattering nanoparticles, and an optical detection system in the housing, where the optical detection system is capable of providing an illuminated electric field, where the illuminating electric field is capable of being used for Raman spectroscopy with the Raman-scattering nanoparticles and the calibration solution to analyze the sample under test input to the cartridge.

In one embodiment of our invention, the calibration standard is an isotope of the analyte under investigation. An isotope is a powerful internal standard as it differs from the analyte only in the number of neutrons. The chemical response and reaction will be nearly identical to the analyte. However, under many forms of spectroscopy, including Raman spectroscopy, the isotope has a different spectrum. Therefore, one can measure the analyte and isotope spectra simultaneously, using ratiometric analysis to quantify the unknown analyte.

An alternative embodiment relies upon an isotopic calibration standard for a compound that is chemically similar to the analyte under study. For example, selenium and sulfur are chemically quite similar. A measurement of selenate may rely upon the measurement of sulfate, of a selenate isotope, or of a sulfate isotope as a calibration standard.

Another embodiment of our invention provides a calibration standard during manufacturing through modification of nanoparticle marker chemistry. Modifications of the marker provide two advantages. First, the modification can be chosen for analyte specificity using compounds designed to interact only with the analyte under investigation. This approach reduces interferences while increasing signal strength. Second, the modification provides a well-defined Raman signal that measures the signal enhancing capabilities of the markers. This signal acts as a calibration standard.

In one aspect of the invention, the chemical compounds can include thiols, amines, silanes, polymeric particles, metallic particles, crown esters, cysteamine, cystamine, diethylaminethanethiol, mercaptopropionic acid, 1-propanethiol, octanethiol, octyldecanethiol, polystyrene, iron, or silica.

According to another aspect of the invention, the calibration solution comprises isotopes of the sample under test.

In a further aspect of the invention, the calibration solution comprises a chemical composition in the sample under test.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the device may be injection molded, constructed of elastomers, or processed using semiconductor methods and materials. The channels may contain curved segments to extend their lengths or may have varying depths to encourage separation. The detection particles could combine multiple signaling and binding mechanisms, such as being magnetic and fluorescent to enhance optical detection within a magnetic field. Example channel shapes and sizes (heights, ratios), materials, electrode configurations, carrier solutions, fabrication methods can be varied without departing from the spirit of the invention. All such variations are considered to be within the scope and spirit of the present invention as defined by the following claims and their legal equivalents.

What is claimed:

1. A hand-held microfluidic testing device comprising:
   a) a housing, wherein said housing comprises a cartridge receiving port;
   b) a cartridge, wherein said cartridge comprises
      i) a sample channel, wherein said sample channel comprises a first sample channel region and a second sample channel region, wherein a cross-section of said first sample channel region is smaller than a cross-section of said second sample channel region;
      ii) a detection region comprising a first detection region and a second detection region, wherein a cross-section of said first detection region is larger than a cross-section of said second detection region and said second sample channel region is connected to said first detection region;
      iii) Raman-scattering nanoparticles wherein said Raman-scattering nanoparticles are larger than said cross-section of said first sample channel region and larger than said cross-section of said second detection region, wherein said Raman-scattering nanoparticles are disposed to collect in said first detection region to form a region of densely packed said Raman-scattering nanoparticles; and,
   c) an optical detection system in said housing, wherein said optical detection system is capable of providing an illuminating electric field, wherein said illuminating electric field is capable of being used for Raman spectroscopy with said Raman-scattering nanoparticles to analyze said sample under test input to said cartridge.

2. The microfluidic testing device of claim 1, wherein said Raman-scattering nanoparticles have a size in a range of 10 nm to 10 μm.

3. The microfluidic testing device of claim 1, wherein said Raman-scattering nanoparticles move when subject to forces selected from the group consisting of electroosmosis, electrophoresis, fluid pressure, moveable wall pressure, undulary electroosmosis, undulary electrophoresis, undulary fluid pressure and undulary moveable wall pressure.

4. The microfluidic testing device of claim 1, wherein said Raman-scattering nanoparticles are selected from the group consisting of gold particles, copper particles, silver particles, magnetic particles, particles having binding chemistry, and quantum dots.

5. The microfluidic testing device of claim 1, wherein said second detection region comprises a sieve structure having openings smaller than said Raman-scattering nanoparticles.

6. The microfluidic testing device of claim 1, wherein said detection region comprises flexible material, wherein said flexible material is operably disposed to form said first sample channel region and said second detection channel region.

7. The microfluidic testing device of claim 1 comprising an input channel disposed to input said Raman-scattering nanoparticles into said second sample channel region.

* * * * *